(12) United States Patent
Godfrin et al.

(10) Patent No.: US 9,125,876 B2
(45) Date of Patent: Sep. 8, 2015

(54) ERYTHROCYTES CONTAINING ARGININE DEIMINASE

(75) Inventors: Yann Godfrin, Lyons (FR); Pierre-Olivier Goineau, Lyons (FR)

(73) Assignee: ERYTECH PHARMA, Lyons (FR)

(*) Notice: Subject to any disclaimer, the term of this patent is extended or adjusted under 35 U.S.C. 154(b) by 363 days.

(21) Appl. No.: 11/912,236

(22) PCT Filed: Apr. 25, 2006

(86) PCT No.: PCT/IB2006/001004
§ 371 (c)(1),
(2), (4) Date: Oct. 22, 2007

(87) PCT Pub. No.: WO2006/114691
PCT Pub. Date: Nov. 2, 2006

(65) Prior Publication Data
US 2008/0274092 A1 Nov. 6, 2008

(30) Foreign Application Priority Data
Apr. 25, 2005 (FR) ...................................... 05 04122

(51) Int. Cl.
*A61K 35/18* (2015.01)
(52) U.S. Cl.
CPC ...................................... *A61K 35/18* (2013.01)
(58) Field of Classification Search
CPC .............. A61K 2300/00; A61K 35/18; A61K 47/48776; G01N 2333/982; G01N 33/555; C12N 5/0641; C12N 11/08; C12N 11/16; C12N 9/82
USPC ........................................................ 435/372
See application file for complete search history.

(56) References Cited

U.S. PATENT DOCUMENTS

| | | | |
|---|---|---|---|
| 4,965,857 A | 10/1990 | Auracher et al. | |
| 5,372,942 A | 12/1994 | McGarrity | |
| 5,916,793 A | 6/1999 | Filpula | |
| 6,737,259 B1 | 5/2004 | Clark | |
| 2006/0002915 A1 | 1/2006 | Min et al. | |

FOREIGN PATENT DOCUMENTS

| | | |
|---|---|---|
| EP | 0 414 007 | 2/1991 |
| GB | 1051382 | 12/1966 |
| JP | 2035081 | 2/1990 |
| JP | 2053490 | 2/1990 |
| JP | 6062867 | 3/1994 |

OTHER PUBLICATIONS

Dong et al Int. J Cancer, 2003, 106(5) 723-728.*
Gong et al Leukemia. May 2000; 14(5):826-9.*
Adriaenssens et al Inter. Jour. Biochemical, 1984, 16 (7), 779-786.*
Dillon et al (Med Sci Monit, 2002; 8(7): 248-253.*
Curley et al., "Regression of hepatocellular cancer in a patient treated with arginine deiminase", Hepatogastroenterology. Sep.-Oct. 2003; 50 (53):1214-6.
Adriaenssens et al., "Hyperargininemia: The Rat As a Model for the Human Disease and the Comparative Response to Enzyme Replacement Therapy With Free Arginase and Arginase-Loaded Erythrocytes In Vivo", pp. 779-786, vol. 16, No. 5, Great Britain.
Thomas et al., "Enzymic degradation of plasma arginine using arginine deiminase inhibits nitric oxide production and protects mice from the lethal effects of tumour necrosis factor and endotoxin", pp. 581-587, Biochemical Society, (2002) 363, Great Britain.
Wei-Chiang, "Arginine Deiminase as an Innovative Anti-Breast Cancer Agent", pp. 1-2, Research Priorities, Innovative Treatment Modalities > New Drug Design: creative science, 2000, University of Southern California.
Gong et al., "Arginine deiminase and other antiangiogenic agents inhibit unfavorable neuroblastoma growth: potentiation by irradiation", pp. 723-728, Int. J Cancer. Sep. 20, 2003; vol. 106 No. 5.
Gong et al., "Arginine deiminase inhibits proliferation of human leukemia cells more potently than asparaginase by inducing cell cycle arrest and apoptosis", pp. 826-829, Leukemia, May 14, 2000.
Vellard, "The enzyme as drug: application of enzymes as pharmaceuticals", pp. 1-7 Current Opinion in Biotechnology, 2003.
Dillon et al., "Biochemical characterization of the arginine degrading enzymes arginase and arginine deiminase and their effect on nitric oxide production", Med. Sci. Monit, pp. 248-253, Basic Research, 2002.
Millan et al, "Drug, enzyme and peptide delivery using erythrocytes as carriers", Feb. 20, 2004, pp. 27-49, vol. 95, No. 1, Journal of Controlled Release, Elsevier, Amsterdam, Netherlands.
Kravtoff et al, "Erythrocytes as carriers for L-asparaginase. Methodological and mouse in-vivo studies", Jul. 1990, pp. 473-476, vol. 42, No. 7, Journal of Pharmacy and Pharmacology, London, GB.
Holtsberg et al, "Poly(ethylene glycol) (PEG) conjugated arginine deiminase: effects of PEG formulations on its pharmacological properties", Apr. 23, 2002, pp. 259-271, vol. 80, No. 1-3, Journal of Controlled Release, Elsevier, Amsterdam, Netherlands.
Park, et al, "Arginine deiminase: A potential inhibitor of angiogenesis and tumour growth", Sep. 1, 2003, pp. 907-914, vol. 89, No. 5, British Journal of Cancer.
Van Broeckhoven et al, "Measurement of Arginine Transport in Human Erythrocytes Using Their Intrinsic Arginase Activity: Implications for the Treatment of Familial Hyperargininemia", 1982, pp. 209-216, vol. 126, Clinica Chimica Acta.
Ash et al, "Structure and Function of Arginases" 2004, pp. 2760S-2764S, The Journal of Nutrition.

(Continued)

*Primary Examiner* — Anoop Singh
(74) *Attorney, Agent, or Firm* — B. Aaron Schulman, Esq.; Stites & Harbison, PLLC.

(57) ABSTRACT

Use of erythrocytes containing arginine deirainase for the preparation of a medicinal product for lowering the plasma concentration of arginine in vivo. The use relates in particular to the treatment of arginine-dependent tumors, such as hepatocarcinoma and malignant melanoma, or inhibition of the synthesis of nitric oxide, and the prevention and/or treatment of septic shock.

8 Claims, 4 Drawing Sheets

(56) References Cited

OTHER PUBLICATIONS

Spector et al, "Comparison or Arginase Activity in Red Blood Cells of Lower Mammals, Primates, and Man: Evolution to High Activity in Primates", 1985, pp. 1138-1145, Am. J. Hum. Genet.

Adriaenssens et al., "Hyperargininemia: The Rat As a Model for the Human Disease and the Comparative Response to Enzyme Replacement Therapy With Free Arginase and Arginase-Loaded Erythrocytes in Vivo", Int.J.Biochem,1984, pp. 779-786, vol. 16, No. 5, Great Britain.

* cited by examiner

ERYTHROCYTES CONTAINING ARGININE DEIMINASE

The present invention relates to the depletion of plasma arginine, to compositions for providing said depletion and to the treatment of pathologies that may benefit from said depletion and its effects, for example on the synthesis of nitric oxide. Thus, the invention relates to the treatment of certain tumors, such as malignant melanoma and hepatocarcinoma, and to the prevention and treatment of septic shock.

All documents, articles and patents or patent applications cited herein are hereby incorporated herein by reference.

Arginine is a nonessential amino acid. It is synthesized in the course of the urea cycle, from citrulline in two stages, owing to the action of argininosuccinate synthetase and argininosuccinate lyase. The first enzyme catalyzes the conversion of citrulline to argininosuccinate and the second performs the conversion to arginine. Arginine is metabolized to ornithine under the action of arginase, and ornithine can in its turn be transformed to citrulline by a reaction catalyzed by ornithine transcarbamoylase.

It has been shown, however, that certain types of tumor cells require arginine to be supplied, and this led to consideration of arginine depression as a possible treatment for these forms of cancers, called arginine-auxotrophic. The antitumor activity of arginine deiminase has been the subject of numerous publications. Thus, in vivo activity has been demonstrated with respect to malignant melanoma and hepatocarcinoma. However, this enzyme has some major drawbacks.

Arginine deiminase is not produced in mammals but is obtained from microorganisms, making it a highly antigenic compound for a mammal.

Moreover, this enzyme has a very short half-life in mammals, of the order of about 5 hours, and must be administered daily at a high dose to become effective. To overcome these drawbacks, the authors proposed pegylated forms of this enzyme, i.e. arginine deiminase conjugated with polyethylene glycol (PEG), which led to less antigenic formulations with a longer half-life (from 7 to 9 days). Among works dealing with this subject, we may mention the following concerning the treatment of melanoma and of hepatocarcinoma: F. Izzo et al., J. Clin. Oncol. 2004, 22: 1815-1822; C. M. Ensor et al., Cancer Research 2002, 62: 5443-5450; F. W. Holtsberg et al. J. Control. Release 2002, 80: 259-271; J. S. Bomalaski et al., Preclinica, Research Article November/December 2003, 1, 5: 284-293; Curley S. A. et al., Hepato-gastroenterology, 50, 1214-6, 2003.

U.S. Pat. No. 4,965,857 proposes an entirely different method, involving extracorporeal treatment of the blood using a reactor in which arginine deiminase acts upon the extracorporeal circulation.

The current treatments based on pegylated arginine deiminase are interesting, but have certain limitations connected with the need to administer relatively large doses repeated at short intervals, as the half-life is still short, and with toxicity connected with repeated administration at high dose, in the long term with a risk of inducing levels of antibodies to the active principle which may lead to allergic effects and inhibition of the active principle.

It would therefore be of considerable benefit to have at our disposal an active product having better bioavailability (better biological activity, prolonged half-life), making it possible to optimize the amount of enzyme administered and lower the toxicity, even in the case of repeated treatments, and limit the risks of immune reaction and clinical allergy.

The advantage of using red blood cells as vectors of medicinal products was suggested long ago. They have natural biocompatibility and, after transfusion, they are completely biodegradable by a known process and have a relatively long half-life in vivo (half-life of the order of about 30 days in man).

Encapsulation of arginase, a natural enzyme of the urea cycle, was proposed and tested within the scope of treatment of hyperargininemic patients exhibiting deficiency of this enzyme in their erythrocytes (C. G. Millan, J. Controlled Release 2004, 95: 27-49; K. Adriaenssens et al., Int. J. Biochem. 1984, 16, 7: 779-786). The aim was to compensate the metabolic and enzymatic deficiencies connected with endogenous arginase deficiency.

Arginase has an alkaline optimum pH at about 9.5, and its activity is low at physiological pH. In contrast, arginine deiminase has an optimum pH of about 6.5, retains more than 70% of its activity at physiological pH, and its affinity for arginine is 1000 times greater than that of arginase: B. J. Dillon et al., Med. Sci. Monit. 2002, 8, 7: 248-253. In that study, concerning inhibition of the synthesis of nitric oxide NO, the authors report strong activity of arginine deiminase on extracellular arginine, but absence of activity on intracellular arginine (macrophages).

NO is a biomediator and is thought to be synthesized essentially from extracellular arginine. Septic shock is mediated by NO and by tumor necrosis factor TNFα. Inhibition of the synthesis of NO has been envisaged as a treatment against septic shock, hence the works of Dillon et al. supra and of J. B. Thomas, Biochem. J. 2002, 363, 581-587. NO also seems to be involved in the cancerization process, as reported in Lind DS. Arginine and cancer. J. Nutr. 2004: 2837S-41.

It appears that arginine deiminase possesses a potential for degradation of arginine and inhibition of NO synthesis far greater than arginase. However, this enzyme would not have intracellular enzymatic activity, the physiological pH is not its optimum pH, it has a short half-life and it is likely to induce an immune reaction.

Starting from this complex situation, the inventors set themselves the aim of proposing a technical solution that provides effective degradation of plasma arginine and/or inhibition of the synthesis of nitric oxide NO.

Thus, the present invention relates to the use of erythrocytes containing arginine deiminase for the preparation of a medicinal product for lowering the concentration of plasma arginine in vivo.

Arginine deiminase is identified under reference EC 3.5.3.6 in IUBMB Enzyme Nomenclature. The enzyme employed can be of natural, synthetic or artificial origin, or obtained by genetic engineering (for example production of the enzyme in a host cell, for example *E. coli*, after integration of a vector expressing the gene coding for the enzyme). Arginine deiminases that can be used are described for example in EP-A-1 011 717, EP-A-0 414 007, U.S. Pat. No. 5,372,942, JP-A-6062867, JP-A-2053490, JP-A-2035081. In an equivalent manner, the invention includes the use of analogues of this enzyme which can notably be enzymes that have been modified in order to increase their enzymatic activity (EP-A-0 981 607).

The objective of the present invention is plasma arginine depletion, which means lowering the concentration of arginine in the plasma. Without wishing to be bound to a theory, it is thought that the plasma arginine enters the treated erythrocytes by passive diffusion. The erythrocytes of the invention behave as bioreactors, in which the arginine that enters is degraded by the arginine deiminase. The invention offers other advantages. At the end of their life, the erythrocytes are destroyed by macrophages, essentially in the liver, the spleen and the bone marrow, as well as in the lungs. This leads to targeted release of arginine deiminase, causing local depletion of plasma arginine. This effect is utilized in the treatment of pathologies, in particular of tumors, that affect these organs, such as hepatocarcinoma.

The solution adopted by the invention makes it possible to combine several decisive advantages in a remarkable way, namely the lifetime of the erythrocytes permitting a long time of action, storage of the enzyme in an environment that is, on the one hand, favorable, with a pH generally below 7.4 at which the enzyme displays an enzymatic activity greater than 80% and, on the other hand, preserved, since the enzyme is isolated from the immune system, thereby reducing the risk of developing an immune reaction to the enzyme, which is a great advantage in the case of repeated treatments. The enzyme is protected from any anti-arginine deiminase antibodies by the membrane of the erythrocytes, and its enzymatic activity is therefore preserved even when antibodies are present in the blood of the patient being treated. Furthermore, healthy cells are preserved, as the enzyme does not act upon intracellular arginine.

The invention therefore finds particularly interesting application in arginine-dependent tumors, for which the favorable effect of plasma arginine depletion has been demonstrated (see for example F. Izzo et al., 2004, C. M. Ensor et al., 2002, F. W. Holtsberg et al., 2002, J. S. Bomalaski et al., 2003, and Curley S. A. et al., 2003, previously cited).

According to a first embodiment of the invention, the medicinal product is intended for the treatment of arginine-dependent tumors. By arginine-dependent we mean tumors involving tumor cells that require arginine for replication, are unable to synthesize some or all of the arginine that they need, and therefore require a supply of arginine. Plasma arginine depletion will deprive these cells of the arginine that is essential for their development, leading to targeted death of these cells, inhibition of tumor growth or regression of the tumor mass.

According to one characteristic, the invention relates to the use of these erythrocytes for the preparation of a medicinal product for treating hepatocarcinoma or primary liver cancer.

According to a second characteristic, the invention relates to the use of these erythrocytes for the preparation of a medicinal product for treating malignant melanoma, in its various forms, such as superficial spreading melanoma and nodular melanoma.

According to a second embodiment of the invention, the invention relates to the use of these erythrocytes for the preparation of a medicinal product for inhibiting the synthesis of nitric oxide. It should be pointed out that the medicinal product acts at least partly via the degradation of plasma arginine, as described in Dillon et al., 2002, cited previously.

According to one characteristic of this embodiment, the invention relates to the use of these erythrocytes for the preparation of a medicinal product for the prevention and/or treatment of septic shock.

The invention further relates to the use of these erythrocytes for the preparation of a medicinal product for the treatment of one of the following forms of cancer:
breast cancer (Shen Wei-Chiang et al., California Breast cancer research
neuroblastoma (Gong H. et al., Int. J. Cancer 2003, 106: 723-8)
leukemia (Gong H. et al. Leukemia 2000, Vol. 14, 826-9; Noh E. J. et al., Int. J. Cancer 2004, 112: 502-8);
or for inhibition of angiogenesis and the treatment of associated diseases such as: angioma, angiofibroma, arthritis, diabetic retinopathy, retinopathy of the premature, neovascular glaucoma, disease of the cornea, involutional and other forms of macular degeneration, pterygium, retinal degeneration, retrolental fibroplasia, psoriasis, telangiectasis, granuloma pyogenicum, seborrheic dermatitis, acne, cancer and metastases connected with angiogenesis (WO0209741; Park I. S. et al., Br. J. Cancer 2003, 89: 907-14).

The invention also relates to erythrocytes containing arginine deiminase.

The invention further relates to a suspension of these erythrocytes in a pharmaceutically acceptable saline solution (generally, standard medium for erythrocytes, solution containing NaCl and one or more ingredients selected from glucose, dextrose, adenine and mannitol; e.g. SAG-mannitol or ADsol). Said solution can provide preservation of the erythrocytes, and it can include a preservative such as L-carnitine. Said suspension can be packaged ready for use or for dilution before use.

The final hematocrit value of the ready-to-use product (after dilution before use, if necessary) is preferably between 40 and 70%. It can be administered intravenously, preferably by perfusion.

Such a suspension or any administrable formulation containing erythrocytes according to the invention constitutes in itself a medicinal product or a pharmaceutical composition covered by the invention. Said medicinal product or composition can notably be intended for the various applications mentioned above. It can be packaged for example as a flexible bag for perfusion, or in some other form for administration by injection.

According to one characteristic of the invention, the medicinal product comprises a suspension of erythrocytes with a hematocrit value between 40 and 70%, preferably between 45 and 55%, and more preferably of 50%. It is preferably packaged in a volume of 10 to 250 ml. The quantity of encapsulated enzyme corresponding to the medical prescription is preferably contained wholly in the bag of blood. A medical prescription can vary from 1 to 200 IU per kg of body weight.

The invention also relates to a method of treatment of arginine-dependent forms of cancer, such as hepatocarcinoma and malignant melanoma, or one of the other cancerous or non-cancerous pathologies mentioned above, comprising the administration of an effective amount of said medicinal product to a patient who needs it, notably by the intravenous route, by injection or perfusion, and preferably by perfusion.

According to an interesting modality, the patient is treated after surgical excision of the tumor.

The invention also relates to a method of treatment intended to inhibit the synthesis of nitric oxide and/or prevent and/or treat septic shock, comprising the administration of an effective amount of said medicinal product to a patient, notably by the intravenous route, by injection or perfusion, and preferably by perfusion.

According to a particularly advantageous modality for these various methods of treatment, the patient is treated with his own erythrocytes, after they have been treated for encapsulation of the enzyme. As a variant, the erythrocytes are obtained from one or more donors.

The method can thus comprise collecting one or more blood samples, for example bag(s) of blood, from a patient or from one or more donors, the preparation of a deposit or concentrate of erythrocytes, enzyme incorporation according to the invention and the production of a batch of erythrocytes incorporating the enzyme, then the administration of the suspension (medicinal product) to the patient, by the intravenous route.

Typically, a volume of suspension of treated erythrocytes corresponding to from 1 to 200 IU of enzyme per kg of body weight is administered. According to one characteristic of the invention, from 10 to 250 ml of a suspension of erythrocytes at a hematocrit value between 40 and 70%, preferably between 45 and 55%, and more preferably of 50%, is administered.

According to a particular modality, such a suspension is administered at a frequency between 15 days and three months, preferably monthly, for a sufficient period of time.

The techniques for encapsulating active principles in erythrocytes are known and the basic technique by lysis-resealing, which is preferred here, is described in patents EP-A-101 341 and EP-A-679 101, to which a person skilled in the art can refer. According to this technique, the primary compartment of a dialyzer is supplied continuously with a suspension of erythrocytes, whereas the secondary compartment contains an aqueous solution that is hypotonic relative to the suspension of erythrocytes in order to lyse the erythrocytes; next, in a resealing unit, resealing of the erythrocytes is induced in the presence of the enzyme by increasing the osmotic and/or oncotic pressure, then a suspension of erythrocytes containing the enzyme is collected.

Among the variants described to date, preference will be given to the method described in French patent application No. 0408667, which provides efficient, reproducible, reliable and stable encapsulation of the enzyme. This method comprises the following stages:

1—suspending packed red blood cells (PRBCs) (or globular concentrate) in an isotonic solution at a hematocrit value greater than or equal to 65%, refrigeration between +1 and +8° C.,
2—measurement of osmotic fragility on a sample of erythrocytes from the same PRBCs, where stages 1 and 2 can be performed in any order (including in parallel),
3—procedure for lysis and internalisation of the enzyme (in particular within one and the same chamber), at a temperature maintained constant between +1 and +8° C., comprising passing the suspension of erythrocytes at a hematocrit value greater than or equal to 65% and a hypotonic lysis solution refrigerated between +1 and 8° C. through a dialysis cartridge; the lysis parameters being adjusted as a function of the osmotic fragility measured previously; and
4—resealing procedure (carried out in particular in a second chamber) in which the temperature is between +30 and +40° C., in the presence of a hypertonic solution. "Internalisation" means penetration of the enzyme inside the erythrocytes.

According to a first characteristic of the invention, the PRBCs are suspended in an isotonic solution at a high hematocrit value, greater than or equal to 65%, and preferably greater than or equal to 70%, and this suspension is refrigerated between +1 and +8° C., preferably between +2 and +6° C., and typically at about +4° C. According to a particular modality, the hematocrit value is between 65 and 80%, and preferably between 70 and 80%.

According to an important characteristic of the invention, the osmotic fragility of the erythrocytes is measured just before the lysis stage. The erythrocytes or the suspension containing them are advantageously at a temperature close to or equal to the temperature chosen for lysis. According to another advantageous characteristic of the invention, once the measurement of osmotic fragility has been obtained it is quickly utilized, i.e. the lysis procedure is carried out very soon after taking the sample. This time delay between taking the sample and commencement of lysis is preferably less than or equal to 30 minutes, and even more preferably less than or equal to 25 or even 20 minutes.

The two parameters permitting dialysis to be controlled are the dwell time of the cells in the dialyzer (as a function of the characteristics of the latter) and the osmolarity of the dialyzate. These two parameters must be adjusted in relation to the characteristics of osmotic resistance, or conversely fragility, of the red blood cells which are processed for undergoing the stages of lysis/resealing. This osmotic resistance can be characterized by at least one of the following parameters:

a. The osmolarity of the medium at which hemolysis appears, i.e. the start of pore formation.
b. The rate V of hemolysis, determined from the slope of the linear portion of the curve % hemolysis=f(osmolarity of the medium).
c. The percentage hemolysis for a given osmolarity.
d. The osmolarity at which 50% hemolysis ($H_{50}$) is obtained.
e. The time taken to obtain a certain percentage of hemolysis (for example 50%).

According to preferred embodiments, the osmotic resistance is characterized by means of the parameters b, d or b and d.

The osmotic fragility must therefore be measured in a short time, compatible with the short time delay between taking the sample and commencement of lysis. According to one characteristic of the invention, one or more of these hemolysis parameters are measured against a hypotonic solution of known isotonicity, e.g. water (distilled water etc.), through a semipermeable membrane. A manual method can be envisaged. However, according to a preferred embodiment of the invention, the osmotic fragility is measured using an automatic measuring instrument that is designed for measuring the osmotic fragility of a sample of erythrocytes in less than 15 minutes, more particularly in less than 12 minutes and preferably in less than 10 minutes, and the result obtained is utilized with a short time delay to adjust the lysis parameters, and begin lysis.

The osmotic fragility can be measured using an instrument that automates, at least in part, the manual technique described by J. V. Dacie in Practical Haematology, 2nd edition, Churchill, London 1956. An example of such an instrument is described in the article by J. Didelon et al., Clinical Hemorheology and Microcirculation 23 (2000) 31-42. The principle is based on the use of a device in which the sample of the suspension of erythrocytes to be evaluated, and a hypotonic solution of known isotonicity, e.g. distilled water, of suitable volumes, are placed on either side of a semipermeable membrane, so as to generate slow hemolysis of the erythrocytes as the NaCl ions diffuse towards the solution, e.g. distilled water. The progress of hemolysis over time is monitored by measuring the transmittance (cf. J. Didelon et al., Biorheology 37, 2000: 409-416) using laser radiation with a wavelength of 808 nm. A photoelectric cell measures the variation in the light transmitted through the suspension. For example, measurements are taken for 10 minutes. The instrument provides one or more of the parameters a-e mentioned above.

According to a first modality, the osmotic fragility is measured on a sample whose initial temperature is between +1 and +8° C., preferably with distilled water also at this temperature, in conditions in which temperature variation does not affect the measurement. According to a second modality, the osmotic fragility is measured on a sample maintained at a temperature between +1 and +8° C. Thus, the measuring instrument described in J. Didelon et al. (supra) can be modified to permit temperature regulation. Said temperature is preferably close to or equal to the lysis temperature.

Once one or more of these parameters have been determined, a relation can be applied that takes into account said parameter or parameters in order to determine either the flow rate of the cells in the dialyzer, or the osmolarity of the dialyzate sufficient to obtain red blood cells encapsulating the enzyme and/or the desired amount of the latter:

$$\text{Flow rate of erythrocytes} = [A \times (H_{50})] + [B \times (V)] + K$$

A and B=variables that can be adapted in relation to the dialyzer and the osmolarity of the lysis solution
K=constant for adjustment.

$$\text{Osmolarity of dialyzate} = [C \times (H_{50})] + [D \times (V)] + K$$

C and D=variables that can be adapted in relation to the dialyzer and the flow rate of erythrocytes in the dialyzer
K=constant for adjustment.

According to one aspect of the invention, the lysis procedure is started when the temperature of the suspension of erythrocytes is between +1 and +8° C., and the osmotic fragility has been measured and the lysis parameters have been recorded.

According to a preferred embodiment, the concentration of NaCl in g/L which brings about 50% haemolysis is measured (parameter d.) and the flow rate of the erythrocyte suspension in the dialysis cartridge is adjusted in accordance with the measured concentration values.

According to an aspect of the invention, the lysis procedure is started when the temperature of the erythrocyte suspension is from +1 to +8° C., and the osmotic fragility has been measured and the lysis parameters recorded.

According to an advantageous characteristic, the initial suspension to be treated is placed in the lysis-internalisation chamber mentioned above. According to one embodiment of the invention, the method employs a refrigerated module equipped with temperature control, and in this module is placed a bag of the suspension of erythrocytes refrigerated between +1 and +8° C., already connected, or which is then connected, to a disposable sterile removable assembly, comprising a dialysis cartridge, tubes for connecting the cartridge to the bag and to the lysis solution, and in addition the module has means for providing circulation of the suspension of erythrocytes and of the lysis solution, the temperature within said module being stabilized at a temperature between +1 and +8° C. The refrigerated module is dimensioned so that it can accommodate the bag and the disposable removable assembly. The arrangement of the bag, the dialysis cartridge, and the lysis solution, connected together by the various tubes, within said single refrigerated module is an advantageous characteristic of the method according to the invention.

The term "bag" refers to the flexible bags or pouches commonly used in the field of blood transfusion and blood derivatives.

According to an important aspect of the invention, steps are taken to maintain the erythrocytes in homogeneous suspension in the bag, so as to maintain a stable hematocrit value of the suspension passing through the dialyzer. According to a characteristic of the invention, the bag is accordingly provided with external circulation in a loop, which provides circulation of the suspension from and to the bag.

"Dialysis cartridge" means an element comprising two compartments separated by a dialysis partition, through which ion exchange can take place, enabling the osmotic pressure of an aqueous solution located in one of the compartments to be altered in a controlled manner by introducing an aqueous solution containing a salt in the other compartment. This type of cartridge is widely used in the medical field. According to a preferred modality, a hollow-fiber dialysis cartridge is used, for example having the following specifications: inside diameter of the fibers between 100 and 400 µm, total external surface of the fibers between 0.3 and 2 m², length of fibers between 10 and 40 cm, coefficient of ultrafiltration between 1.5 and 8 ml/h·mmHg.

As already mentioned, the lysis procedure can be started when the temperature of the suspension in the bag is between +1 and +8° C. According to an interesting modality, the temperature of the suspension is controlled by means of a sensor located on the external loop circulation.

Depending on the osmotic fragility determined, action can be taken on two main parameters, the flow rate of the suspension of erythrocytes in the dialysis cartridge and the osmolarity of the lysis solution, it being preferable to set, in both cases, a constant flow rate for the lysis solution. The value of the flow rate is not critical. Typically, for a hollow-fiber dialysis cartridge as described above, the flow rate of the lysis solution is set between 50 and 300 ml/min, and preferably between 150 and 250 ml/min.

The lysis solution is a saline solution that is hypotonic relative to the suspension of red blood cells. When it is set to a constant value, its osmolarity can typically be between 20 and 120 mOsm, preferably between 70 and 110 mOsm, for example of the order of 90 mOsm.

As an example, the lysis solution can comprise $Na_2HPO_4$ and/or $NaH_2PO_4$ and a sugar such as glucose.

According to a first modality, the flow rate of the suspension of erythrocytes through the dialysis cartridge is adjusted, whereas the flow rate and osmolarity of the lysis buffer are fixed. Higher osmotic fragility means higher flow rate of the suspension. Typically, for a cartridge with the specifications stated above, the flow rate will need to vary in the range from 5 to 200 ml/min, preferably from 10 to 40 ml/min.

According to a second modality, the osmolarity of the lysis solution is adjusted, whereas the flow rates of the suspension and of the lysis solution are fixed. Higher osmotic fragility means increasing the osmolarity of the lysis solution. Typically, the osmolarity will need to vary in the range from 10 to 200 mOsm/l, preferably from 20 to 150 mOsm/l.

According to a third modality, both the flow rate of the suspension of erythrocytes through the dialysis cartridge, and the osmolarity of the lysis solution are adjusted.

The enzyme to be encapsulated can be present in the bag of suspension and/or can be introduced, preferably gradually, in the circulation of suspension upstream or downstream of the dialysis cartridge. As the volumes introduced are small, refrigeration of the enzyme is optional.

Preferably, the suspension of red blood cells is produced from PRBCs of a blood group compatible with the recipient, deleukocytized, without listed pathogen, notably presented in a bag, for example of 500 ml. The red blood cells may have been irradiated when they are intended for highly immunodepressed patients liable to display a graft/host immune reaction (R. J. Davey, Immunol. Invest. 1995, 24 (1-2): 143-149).

According to a particular feature of the invention, the initial PRBCs, used for preparing the suspension, were treated beforehand to remove elements from the blood other than the erythrocytes. This type of treatment, for example washing with a saline solution to remove the plasma or a preserving solution, is known by a person skilled in the art.

According to a particular modality, washing is carried out in the presence of the enzyme to be encapsulated.

Washing can be carried out by any usual technique, such as the quadruple-bag or 4-bag technique for the washing of red blood cells (MacoPharma method and transfer bag). It is also possible to use an automatic red blood cell washer of the type COBE 2991 Cell Processor.

According to another characteristic of the invention, the erythrocytes can be treated beforehand with a solution for increasing and/or homogenizing their osmotic resistance. Such solutions are known by a person skilled in the art. For example, a solution containing L-carnitine can provide an improvement of the osmotic resistance of the red blood cells. As other examples, we may mention solutions of heparin, of citrate-phosphate-dextrose (CPD) and of mannitol.

The temperature during the lysis stage is preferably maintained between +2 and +6° C., and even more preferably around +4° C.

The resealing process is preferably effected by heating the lysed suspension and adding a hypertonic resealing solution. The resealing temperature can be between +30 and +40° C. It is preferably between +35 and +38° C., for example about 37° C. Incubation can typically last for 15 to 45 minutes.

Preferably, the suspension leaving the dialysis cartridge as well as a hypertonic resealing solution are introduced, preferably continuously, into an intermediate bag. There the suspension is heated, and incubated at the desired temperature for a sufficient time to ensure resealing. According to a particular aspect, the intermediate bag is placed in a heated module or container, the interior temperature of which is regulated to the chosen temperature.

As a variant, the suspension and the resealing solution are introduced into an intermediate bag. When all of the suspension has been collected in this bag it is sealed and transferred to a module for heating and incubation at the desired temperature.

The suspension of resealed red blood cells can then undergo one or more stages of washing with a saline solution, in order to remove cells that were poorly resealed or not resealed, residues and extracellular hemoglobin.

According to another characteristic, the erythrocytes are packaged in an erythrocyte storage solution, for example containing L-carnitine.

The erythrocytes produced are preferably stored at a temperature between +1 and +8° C., preferably between +2 and +6° C., typically at about +4° C.

The final hematocrit value of the product is preferably between 40 and 80%, typically between 40 and 70%.

The present invention can be implemented using a lysis-resealing device comprising:
- a module that can be refrigerated at a temperature between +1 and +8° C., comprising refrigerating means and temperature regulating means,
- a disposable sterile removable assembly, designed for fitting in the module and comprising a dialysis cartridge that can be connected on the one hand to a feed of lysis solution and on the other hand to a feed of suspension of erythrocytes,
- means for controlling the flow rate of the suspension of erythrocytes through the lysis cartridge and/or adjusting the osmolarity of the lysis solution, as a function of the osmotic fragility of the erythrocytes to be treated.

According to one embodiment, the removable assembly is a disposable kit and comprises a bag for containing the suspension of erythrocytes and a tube connecting said bag to the dialysis cartridge, and the module comprises a pump that works in conjunction with said tube to circulate the suspension of erythrocytes from the bag to and through the cartridge, said pump being optionally coupled to flow regulating means. The assembly ensures that sterility is maintained.

According to an advantageous characteristic, the bag is additionally equipped with a tube with both of its ends connected in a loop to the bag, and the module contains a pump that works in conjunction with said tube to provide circulation of the contents of the bag from and to said bag.

According to another advantageous characteristic, a temperature sensor is arranged on said loop of tube.

According to another characteristic, an enzyme injection tube is connected to the tube connecting the bag to the "blood" inlet of the dialysis cartridge.

According to another characteristic, the dialysis cartridge is connected by a tube to a bottle that can contain the lysis solution and the refrigerated module contains means for receiving said bottle and a pump that can operate in conjunction with said tube to circulate the lysis solution to and through the dialysis cartridge.

According to one characteristic, the refrigerating and temperature controlling means are able to maintain a temperature between +2 and +6° C., and preferably of the order of +4° C. in the module.

According to another characteristic, the "blood" outlet from the dialysis cartridge is connected to an outlet tube leading, or which can lead, to the exterior of the module. According to another characteristic, a tube for injection of active principle is connected to said outlet tube. The outlet tube can be connected to a second bag (intermediate bag) that is able to collect the suspension of erythrocytes after lysis as well as a resealing solution (preferably introduced via a secondary tube opening into the outlet tube a little upstream of its opening into the intermediate bag). Said bag is advantageously arranged in a second module equipped with means of controlling the temperature in said module between +30 and +40° C., preferably between +35° C. and +38° C.

According to an advantageous embodiment, the disposable removable assembly contains all of the following: the bags, circulation tubes, injection tubes (equipped with an injection device or a receptacle that is intended to operate in conjunction with such a device), dialysis cartridge, and preferably a bottle of lysis solution.

Preferably, the removable assembly does not itself have specific means intended for refrigeration or heating. These functions are only provided by the modules or chambers in which the two parts of the assembly are placed.

The pumps used in the method and the device of the invention are preferably peristaltic pumps; according to one embodiment, the pump providing recirculation of the suspension from and to the initial bag and the pump for circulating the lysis buffer have a predetermined constant rotary speed, whereas the pump sending the suspension to the dialysis cartridge has a rotary speed that is controllable as a function of the osmotic fragility of the erythrocytes to be treated.

The enzyme can be introduced by any suitable means, for example a fixed-flow syringe pump, optionally driven, connected to the corresponding injection tube. As a variant, the syringe pumps can be replaced with peristaltic pumps.

The device includes means of controlling the flow rate of the suspension of erythrocytes through the lysis cartridge and/or adjustment of the osmolarity of the lysis solution, as a function of the osmotic fragility of the erythrocytes to be treated.

According to one characteristic, the flow regulating means are designed to control the pump sending the suspension to the dialysis cartridge. According to another, alternative characteristic, the regulating means are designed for regulating the osmolarity of a lysis solution, either by dilution to lower the osmolarity, or to increase said osmolarity by introducing a suitable solute. As a variant, a lysis solution of osmolarity adjusted to the osmotic fragility of the erythrocytes to be treated is introduced into the module.

According to a preferred modality, the device comprises electronic means for controlling the lysis process and optionally the resealing process, in accordance with instructions entered by the operator (e.g. data concerning the flow rate of the suspension of erythrocytes are entered by the operator directly), or in accordance with data entered by the operator, relating to the osmotic fragility (the electronic means then being designed for determining and adjusting the lysis parameters, e.g. the flow rate of the suspension of erythrocytes). Said electronic means are preferably connected to temperature sensors (for controlling the temperature in the modules and/or at the temperature sensor for the suspension of erythrocytes). Said means can control and operate the pumps, for example the pressure and the flow rate of the suspension through the dialysis cartridge.

Preferably, the modules are equipped, on one face at least, with a glass surface, for visual control of the installation and the circulation of the solutions and suspensions.

The invention will now be described in more detail on the basis of embodiments that are used as non-limiting examples, referring to the drawings in which:

FIGS. 4 and 5 represent graphs relative to the pharmacokinetics in the red blood cells for arginine and citrulline concentrations.

RBC or BC is used herein to designate red blood cells.

EXAMPLE 1

Installation

Figure 1:
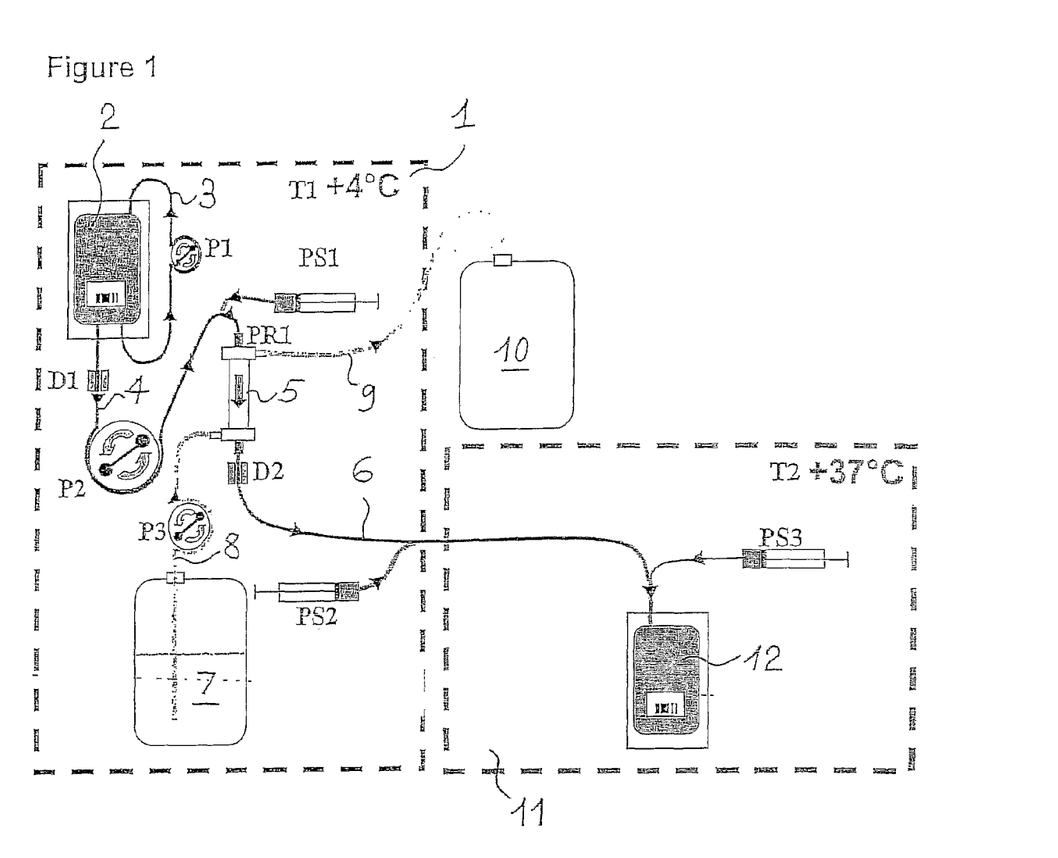
FIG. 1 is a schematic representation of a lysis-resealing device according to the invention.

Reference will first be made to FIG. 1. A first box shown by dashed lines depicts a first module 1, having an overall shape of a parallelepiped, with a glass-covered front (not shown), arranged so that it can be opened and closed. At the back of this module there are peristaltic pumps P1, P2 and P3, and means, not shown, for receiving a removable assembly that will now be described. Pumps P1 and P3 have a predetermined, constant delivery. Pump P2 is controlled so that its delivery varies.

The removable assembly includes a bag 2 that is flexible in volume, containing a suspension of erythrocytes to be lysed. Said bag 2 is equipped with a flexible tube 3, in a loop, operating in conjunction with pump P1, to provide circulation from and to the bag to maintain the erythrocytes in suspension. Said bag is in addition connected at its base to a flexible tube 4 connected to the inlet of the "blood" compartment of a dialysis cartridge 5. Said tube 4 operates in conjunction with pump P2, which provides circulation of the suspension from the bag to the cartridge. A driven syringe pump PS1 is connected to tube 4 upstream of cartridge 5, and said syringe pump permits the enzyme to be introduced into the circulation of erythrocytes. The outlet of the "blood" compartment of cartridge 5 is connected to an outlet flexible tube 6, which opens onto the exterior of module 1. A second driven syringe pump PS2 is connected to tube 6, and this syringe pump permits the enzyme to be introduced into the circulation of lysed erythrocytes. A bottle 7 containing a lysis solution is arranged in module 1, and is connected to the "dialyzate" inlet of cartridge 5 by a flexible tube 8, which operates in conjunction with pump P3 to provide circulation of the lysis solution through cartridge 5. Finally, the lysis solution leaving the cartridge is removed from module 1 by a flexible discharge tube 9, which ends in a bottle 10 located outside of module 1.

Outlet tube 6 goes into a second module 11 with the overall shape of a parallelepiped, with a glass-covered front (not shown), arranged so that it can be opened and closed. At the back of this module there are means, not shown, for receiving elements forming part of the removable assembly that has just been described partially. Said elements comprise a flexible bag 12, connected to tube 6, and in which the lysed suspension will be stored. A driven syringe pump PS3 is connected to tube 6, for injecting the resealing product.

The removable assembly is made entirely of flexible, transparent plastic, so that the process is completely visible.

Figure 2:
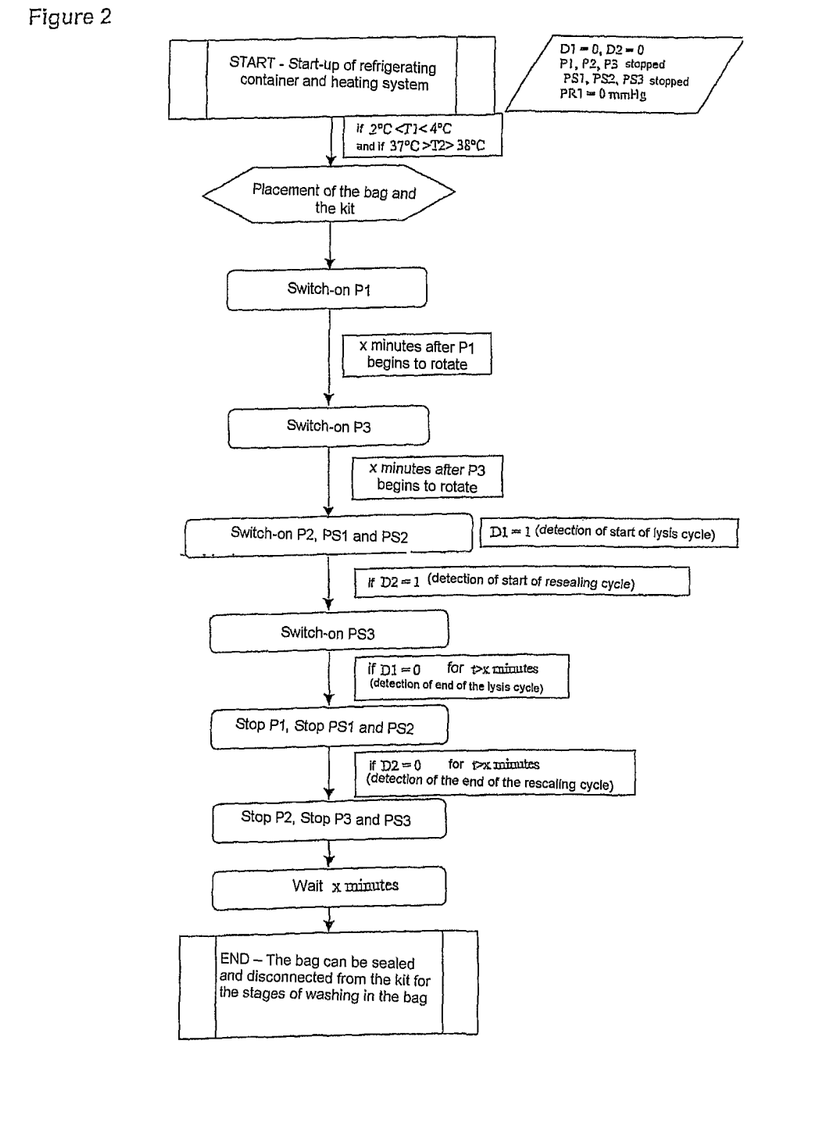
FIG. 2 is a flow chart of the method.

The device is further provided with various means that are not shown:

means for cooling the interior of module 1 and regulating its temperature between +2 and +4° C., comprising, among other things, a temperature sensor located on tube 3 for measuring the temperature of the suspension circulating therein, and a temperature sensor for measuring the temperature T1 inside module 1, module 11 is further provided with means of heating the interior of module 11 and regulating the temperature T2 therein between +37 and +38° C.; a temperature sensor is fitted inside the module.

means (for example ultrasonic or calorimetric) for detecting the presence of erythrocytes in the tubes, at D1 and D2, means PR1 for measuring the pressure at the inlet of the dialysis cartridge.

electronic device receiving on the one hand data arriving from the temperature and pressure sensors and the detecting means, and on the other hand data relating to the settings of the lysis parameters; on the basis of said data, the device controls pumps P1, P2 and P3. A process flow chart is shown in FIG. 2.

The electronic device comprises a computer, designed for executing the above flow chart.

Implementation of said device leads to the recovery, at 12, of a bag containing a suspension of erythrocytes containing the enzyme.

EXAMPLE 2

Production of Erythrocytes Encapsulating Arginine Deiminase 400 ml of blood is taken from the patient. The blood, maintained at 4° C., is deleukocytized and washed with a saline solution to remove the plasma, and placed in a flexible bag with a volume of 250 ml, at a hematocrit adjusted to 80%.

An aqueous solution of arginine deiminase is added to the suspension of erythrocytes so as to obtain a concentration of 400 IU of enzyme per ml and a hematocrit of 70%.

Take 1 ml of the suspension at 4° C. and place it in the instrument for measuring osmotic fragility described in J. Didelon et al. 2000 cited previously, the operating principle of which was described above. Measurements are taken for 10 minutes. The instrument makes it possible to determine the salinity that gives 50% hemolysis. This salinity is generally between 3 and 5.5 g NaCl per liter.

The 250-ml capacity flexible bag 2, containing the suspension of erythrocytes and the enzyme, is placed in the installation of Example 1, and the suspension and the hypotonic lysis solution are admitted gradually into the respective compartments of the dialysis cartridge. The flow rate of the suspension of erythrocytes in the dialyzer is controlled between 15 and 30 ml/min, as a function of the salinity parameter determined in the preceding stage (osmotic fragility or resistance).

The resealing solution is added in line at 10% v/v to the suspension of lysed erythrocytes just upstream of bag 12. The suspension is incubated for 30 min at 37° C. in the bag. It is then washed with a saline solution, a preserving solution is added to it (SAG-mannitol), then the bag is stored at +4° C. until it is used.

The method makes it possible to obtain erythrocytes having an enzymatic activity between 80 and 180 IU per ml of pure erythrocytes.

The total volume of the suspension is administered to the patient by intravenous perfusion in accordance with the usual practice of blood transfusion.

EXAMPLE 3

In Vitro Assay

Arginise deimainase is an arginase catabolizing enzyme transforming arginine into citrulline and ammoniac. The aim of the study was to observe and confirm the depletion activity of arginine deiminase obtained from *Pseudomonas aeruginosa* once encapsulated into red blood cells. In this purpose, arginine deiminase-loaded red blood cells were incubated with arginine containing buffer. Citrulline and arginine levels were subsequently assessed by HPLC MS MS method.

Preparation of Arginine Deiminase Loaded Red Blood Cells (RBC)

Solution of recombinant SeMet-containing L-Arginine deiminase (ADI) (120 Ul/ml) originated from *Pseudomona aeruginosa*.

Fresh heparinized OF1 mouse blood was obtained from Charles River laboratories and centrifuged (800 g. 10 min at 4° C.) to remove plasma and buffy coat. Packed erythrocytes were washed 3 times (1:1 v/v) with NaCl 0.9% (800 g, 10 min at 4° C.). After the final washing erythrocytes were mixed with (CGR-ADI) or without (CGR-LR) 20 Ul/ml arginine deiminase and the haematocrit of the RBC suspension was adjusted to 70% (using ADI solution or saline).

Lysis of erythrocytes was obtained by a continuous flow dialysis process into a dialysis bag (cutoff 10 Kd). The hypotonic step was performed at 4° C. during 60 minutes against an adequate volume of lysis buffer at 40 mOsm/l ($NaH_2PO_4$, $2H_2O$ 0.73 g/l; $Na_2HPO_4$, $12H_2O$ 5.035 g/l; glucose 0.36 g/l). 100 ml of hypotonic solution were added for 1 ml of erythrocytes introduced. After collection, the suspension of lysed erythrocytes was incubated at 37° C. for 10 min. The cells were then resealed and annealed by incubation at 37° C. during 30 minutes in a 1/10 (v/v) of resealing solution (adenine 0.39 g/l; inosine 15.6 g/l; sodium pyruvate 6.4 g/l; $NaH_2PO_4$, H20 4.9 g/l; $NaHPO_4$, $12H_2O$ 10.9 g/l, glucose 11.5 g/l; NaCl 50 g/l). After resealing the erythrocytes were washed 3 times (800 g, 10 min at 4° C.) in Tris 310 mOsm/l pH 7.4, BSA 4%.

Whole blood, RBC suspension before and after dialysis step were monitored for haematocrit (Ht), mean cell volume (MCV), mean cell haemoglobin (MCHC) and mean corpuscular haemoglobin concentration (MCHC) using a Cobas Micros 601 CS 14/12 cell counter. CGR-ADI and CGR-LR suspension were at 25% haematocrit after dialysis.

Aliquots of RBC suspension (with or without ADI) were collected before and after dialysis step for subsequent ADI activity measurement.

Assay of ADI Activity

Assay of ADI activity was performed on aliquots of RBC suspension (CGR-ADI and CGR-LR) collected before and after dialysis.

Haematocrit of CGR-ADI and CGR-LR aliquots before dialysis were adjusted from 70% to 40% by an adequate dilution in NaCl 0.9%. Haematocrit of CGR-ADI and CGR-LR aliquot suspension after dialysis was of 25% and wasn't modified. The rate of ADI encapsulated was determined by measurement of ADI activity in whole blood or in supernatant. To determine ADI activity in whole blood, one third of RBC suspension aliquot was frozen in liquid nitrogen during 5 minutes and warmed at 37° C. and 10 µl of a 10 fold dilution in 50 mM MES of frozen RBC was then used for enzymatic assay activity. To determine the enzymatic activity outside red cells, the other two-third of RBC suspension were centrifuged at 4° C. during 10 minutes and 10 µl of a 2 fold dilution in 50 mM MES of supernatant was used for enzymatic assay. The amount of citrulline formed in 10 min was quantified by the calorimetric assay of Prescott and Jones. The standard assay mixture contained 900 µl MES buffer 0.1M pH 6.0, $MgCl_2$ 20 mM and 10 µl of supernatant or frozen RBC sample. The reaction was started by addition of 1 ml 10 mM L-arginine and was allowed to continue for 5, 10, 15 or 20 min at 37° C. The reaction was stopped at theses different times by the addition of 1 ml of an antipyrine-diacetylmonoxime solution. The mixture was boiled during 20 minutes and the absorbance at 466 nm was measured. Standard curves were constructed by appropriately diluting a stock solution of citrulline. Activity of ADI between 15 and 20 min was defined as micromoles of citrulline formed per min of enzyme. All measures were done in duplicates.

In Vitro Functionality Assay in vitro assay was completed by incubating arginine deiminase-loaded red blood cells (CGR-ADI) in a buffer containing arginine and observing the levels of both arginine and citrulline aminoacid. Control of the reaction was realized with red blood cells loaded without arginine deiminase (CGR-LR) incubated in the same conditions.

1 ml of prewarmed arginine deiminase-loaded red cells (CGR-ADI) were mixed with 1 ml of buffer containing 300 µM arginine, 20 mM $MgCl_2$ in Tris pH 7.4. Tris buffer was prepared at 320 mOsm/kg, pH 7.4. The control assay was performed by mixing in the same conditions an equivalent amount of CGR-LR with arginine containing buffer. Mixing was realized by upside down movements. 400 µl of sample, representing time 0, were immediately collected in an ependorf tube and placed at 4° C. The rest of the mixture was incubated during 30 minutes at 37° C. At the end of the reaction, 400 µl representing time 30 (for 30 minutes) were collected in an ependorf and placed at 4° C. For all the samples of 400 µl collected, three quarter (300 µl) were centrifuged at 4° C. during 10 min. After centrifugation, an aliquot of 100 µl of supernatant was collected and frozen at −20° C. The other quarter was directly frozen in liquid nitrogen during five minutes. After warming at 37° C., an aliquot of 50 µl of sample was collected and frozen at −20° C.

Arginine and citrulline levels in each sample were then assessed by HPLC/MS/MS method.

Results: See FIG. 3

Figure 3:
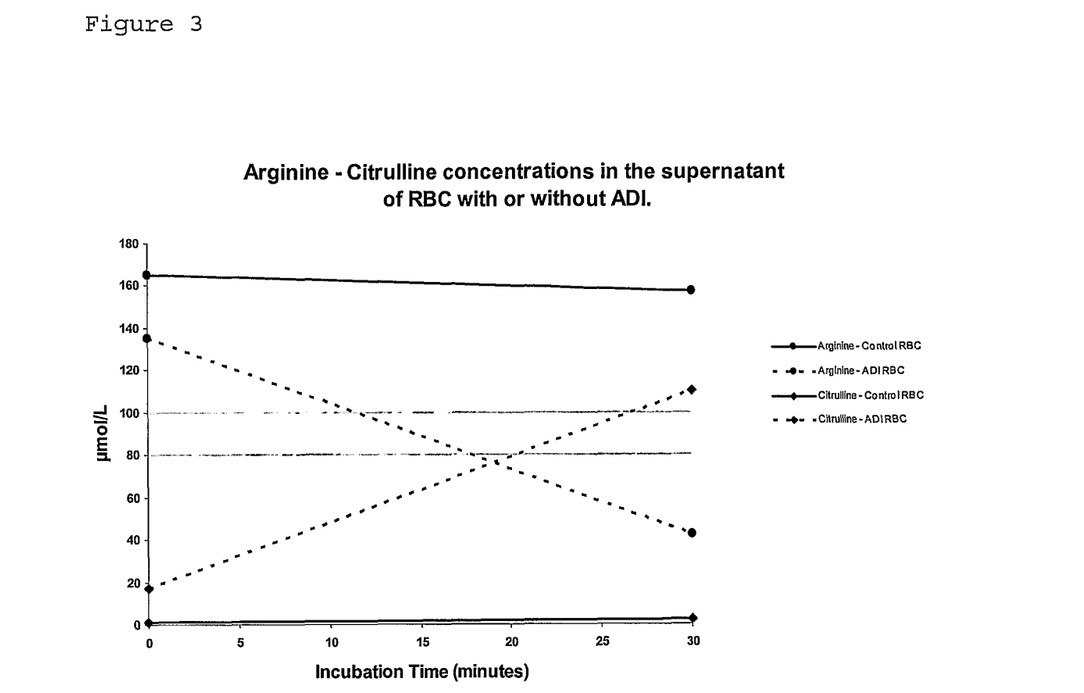
FIG. 3 is a graph illustrating the arginine versus citrulline concentrations in the supernatant of red blood cells with or without ADI (arginine deiminase)

Within 30 minutes at 37° C., the RBC entrapping ADI are able to deplete the arginine contained in the medium (supernatant) from about 135 µmol/L to about 42 µmol/L. In the same time, citrulline concentration in the medium (extra-erythrocytes) is produced from about 17 to about 110 µmol/L. The activity of ADI in the supernatant was under the limit of detection (<0.1 Ul/Ml). The activity measured in the RBC pellet was 2.56 UI/mL. It proves that the arginine deimination is provided by the intra erythrocyte ADI, and that arginine enter into the erythrocyte to be digested into them. In addition, it strongly suggests the citrulline produced into the erythrocyte is going to the extra RBC medium though the red cell membrane.

Concerning the Control RBCs, which are processed erythrocytes where ADI is replaced by saline, arginine from the extra RBC medium decreases only from about 165 µmol/L to about 157 µmol/L within 30 minutes at 37° C., and citrulline reaches only from about 1 to about 2 µmol/L. This low depletion can be explained by the endogenous activity of arginase contained into the RBCs. We underlined again arginase do not produce citrulline while arginine digestion, which is specific to ADI.

EXAMPLE 4

Kinetic Study of Arginine Concentration in Mice Plasma in Response to Injections of Two Formulations of Arginine Deiminase The aim of the study was to follow the plasma pharmacokinetic of arginine and citruline in OF1 mice in response to injection of arginine deiminase-loaded erythrocytes
Preparation of Test and Control Substances Recombinant SeMet-containing L-Arginine deiminase (ADI) (120 UI/ml) originated from *Pseudomona aeruginosa*.

Free arginine deiminase (ADI+RBC) was diluted in washed mouse red blood cells (RBC) and Sag-mannitol 1/3 (v/v) (Haemonetics) in order to obtain a final concentration at 10 UI/ml of packed RBC at hematocrit of 50%. Sag-mannitol was supplemented with 10 mM $MgCl_2$ prior to addition.

Test substance (ADILE) consisted in arginine deiminase loaded red blood cells (RBC). The procedure of preparation of arginine deiminase loaded red blood cells was determined as described for in vitro functionality test of ADI. Before dialysis ADI was mixed with washed packed erythrocytes in order to have a final concentration 50 UI/ml. After dialysis, encapsulated RBC were mixed with Sag-Mannitol 1/3 (v/v) supplemented with 10 mM $MgCl_2$. Final hematocrit was adjusted to 50%. The ADI activity obtained after encapsulation was of 8.35 UI/ml of encapsulated RBC at hematocrit of 50%.

A third sample with no enzyme (CGR) was prepared with washed RBC resuspended with Sag Mannitol (supplemented with 10 mM $MgCl_2$) at final hematocrit of 50%. Saline solution was added in replacement of ADI.

During whole experiment, whole blood, RBC suspension before and after dialysis step were monitored for haematocrit (Ht), mean cell volume (MCV), mean cell haemoglobin (MCHC) and mean corpuscular haemoglobin concentration (MCHC) using a Cobas Micros 601 CS 14/12 cell counter. Aliquots of RBC suspension were collected before and after dialysis step for subsequent ADI activity measurement. ADI activity measurement was determined as described previously.
Animals 64 OF1 female mice, 5-6 week-old and weighing 18-22 g were obtained from Charles River Laboratories (L'Arbresle, France). Animals were observed for 7 days in a specific-pathogen-free (SPF) animal care before treatment. The experimental protocols were approved by the French Ministries of Agriculture and Research. The 64 healthy OF1 mice were randomized in 1 group of 4 mice and 3 groups of 20 mice. Treated mice received a single injection by intravenous route in an injection volume of 250 µl.
Treatment Schedule The treatment schedule was chosen as followed: mice from group 1 were not treated; mice from group 2 were treated by mouse red blood cells washed at hematocrit of 50% (RBC); mice from group 3 received a single injection of arginine deiminase loaded-erythrocytes (ADILE); mice of group 4 received a single injection of free arginine deiminase (ADI+RBC) in suspension in mouse RBC washed at hematocrit of 50%. The different product samples were administered in double blind.

After treatment, mice were sacrificed by cardiac puncture. Isoflurane Forene (Centravet, Bondoufle, France) was used to anaesthetize the mice before sacrifice. The sacrifice of mice was performed as described below in the table. Approximately 800 µl of whole blood were collected in heparin lithium glass tubes and kept immediately in ice-water bath after collection. Blood samples were immediately centrifuged at 2,500 g for 10 min at +4° C. to obtain plasma. About 200 µl of plasma were transferred into propylene tubes, immediately frozen at −20° C. The remaining blood cell pellet was transferred into propylene tubes, immediately frozen at −20° C. until analysis. The levels of arginine and citrulline were measured in one vial of plasma and blood cell pellet.
Amino Acids Analyses Concentration of arginine and citrulline in plasma and blood cell pellets were measured after extraction of arginine and citrulline by HPLC/MS/MS method.

| Treatments | Dose ADI (UI/kg) | Administration route | Sampling times hours | No mice |
|---|---|---|---|---|
| None | 0 | NA | NA | 4 |
| RBC | 0 | IV (10 ml/kg) | 3 | 4 |
|  |  |  | 6 | 4 |
|  |  |  | 12 | 4 |
|  |  |  | 24 | 4 |
|  |  |  | 48 | 4 |
| ADILE | 100 | IV (10 ml/kg) | 3 | 4 |
|  |  |  | 6 | 4 |
|  |  |  | 12 | 4 |
|  |  |  | 24 | 3 |
|  |  |  | 48 | 3 |
| ADI + RBC | 100 | IV (10 ml/kg) | 3 | 4 |
|  |  |  | 6 | 4 |
|  |  |  | 12 | 4 |
|  |  |  | 24 | 4 |
|  |  |  | 48 | 4 |

NA: Not Applicable

Results: See FIGS. 4-5
1) considering the dosage of arginine in a red blood cell pellet, it is observed a strong and rapid decrease in concentration in the mice which received ADI free or entrapped. No significant modification was observed in mice who received normal RBC. However, within 12 hours the concentration in arginine come back to the normal values for the ADI free group (ADI+RBC) and is maintained very low during at least 48 hours for the Entrapped ADI (ADILE).
2) In the same time arginine is depleted, citrulline is produced. However, it is observed while the high level is maintained for ADILE up to 48 hours, it come back to the normal value within 24 hours for the ADI+RBC group. No significant modification was observed in mice who received normal RBC.

Figure 4:
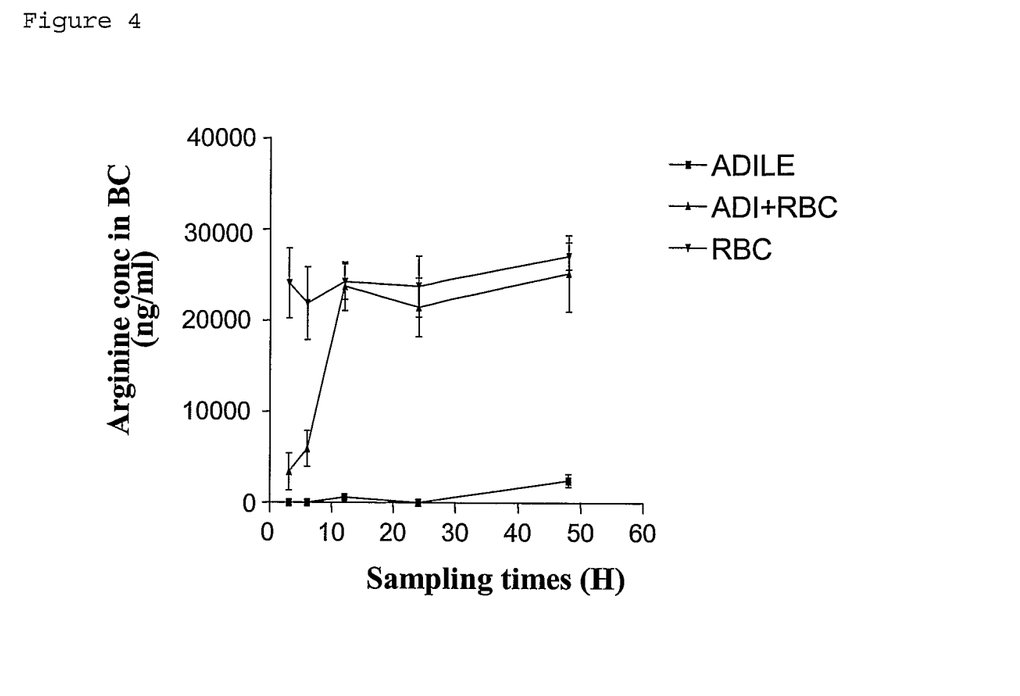
FIG. 4 shows the variation in arginine concentration during time (up to 48 hours after treatment) and FIG. 5 shows the variation in citrulline concentration during time (up to 48 hours after treatment) for three groups of mice treated with: ADILE (arginine deiminase loaded red blood cells), ADI (free arginine deiminase)+RBC, or RBC.
Figure 5:
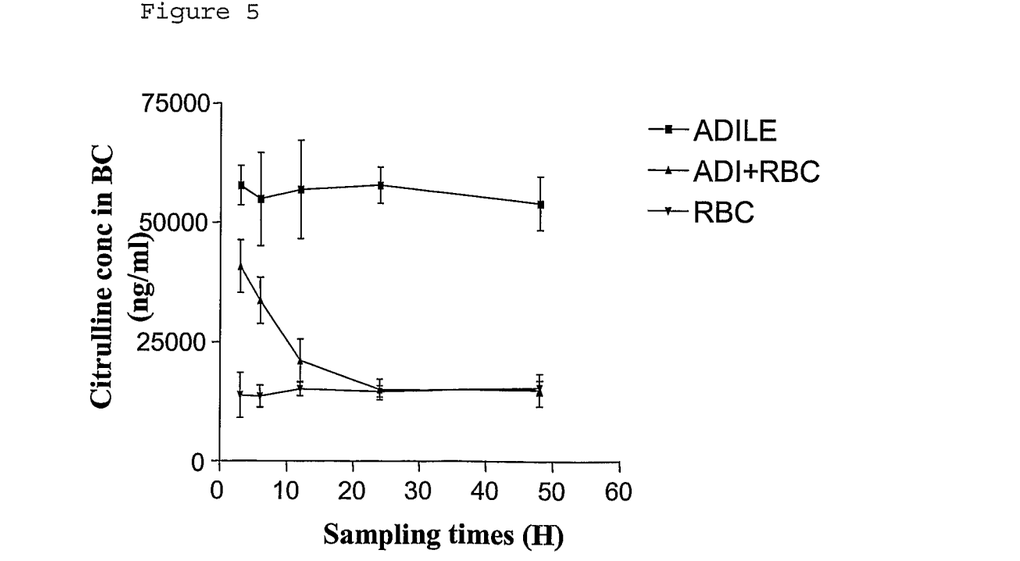

This prove the entrapment of ADI into RBC is possible by lysis/resealing steps, and that the ADI loaded into RBC is much longer efficient than ADI in free solution.

The invention claimed is:

1. A method for lowering the concentration of plasma arginine in vivo in a patient in need thereof comprising:
   (a) providing a composition comprising a suspension of erythrocytes encapsulating arginine deiminase (ADI) having enzymatic activity, wherein said erythrocytes of said suspension are obtained from said patient or from one or more donors whose blood group is compatible with said patient, and wherein said encapsulation prolongs the half-life of the arginine deiminase; and
   (b) intravenously administering to a patient in need thereof an effective amount of said composition, thereby lowering the plasma arginine concentration in said patient beyond 24 hours after administration of the composition; wherein (i) said erythrocytes encapsulating arginine deiminase having enzymatic activity are present in the patient's circulating blood, (ii) the patient's plasma arginine enters the inside of said erythrocytes encapsulating arginine deiminase having enzymatic activity, and (iii) the plasma arginine entered inside said erythrocytes is degraded by the arginine deiminase.

2. The method as claimed in claim 1, wherein said administering is to a patient that requires treatment of an arginine-dependent tumor.

3. The method as claimed in claim 2, wherein said administering is to a patient that requires treatment of hepatocarcinoma.

4. The method as claimed in claim 2, wherein said administering is to a patient that requires treatment of malignant melanoma.

5. The method as claimed in claim 1, wherein said administering is to a patient that requires inhibiting the synthesis of nitric oxide.

6. The method as claimed in claim 1, wherein said administering is to a patient that requires treatment of septic shock.

7. The method as claimed in claim 2, wherein said administering is to a patient that requires treatment of breast cancer, neuroblastoma or T-cell lymphoblastic leukemia.

8. The method as claimed in claim 1, wherein said administering is to a patient that requires inhibition of angiogenesis or treatment for an angiogenesis associated disease.

* * * * *